United States Patent
Kurnadi et al.

(10) Patent No.: US 10,215,717 B2
(45) Date of Patent: Feb. 26, 2019

(54) DETECTION OF AN OBJECT WITHIN A VOLUME OF INTEREST

(71) Applicant: Decision Sciences International Corporation, Poway, CA (US)

(72) Inventors: Priscilla Kurnadi, San Diego, CA (US); Shawn McKenney, Ramona, CA (US); Sean Simon, Vista, CA (US); Peter Lam, San Diego, CA (US)

(73) Assignee: Decision Sciences International Corporation, Poway, CA (US)

( * ) Notice: Subject to any disclaimer, the term of this patent is extended or adjusted under 35 U.S.C. 154(b) by 223 days.

(21) Appl. No.: 14/839,883

(22) Filed: Aug. 28, 2015

(65) Prior Publication Data

US 2016/0061752 A1    Mar. 3, 2016

Related U.S. Application Data

(60) Provisional application No. 62/043,323, filed on Aug. 28, 2014.

(51) Int. Cl.
| | |
|---|---|
| *G01J 1/42* | (2006.01) |
| *G01T 1/00* | (2006.01) |
| *G01N 23/046* | (2018.01) |
| *G01V 5/00* | (2006.01) |

(52) U.S. Cl.
CPC ......... *G01N 23/046* (2013.01); *G01V 5/0016* (2013.01)

(58) Field of Classification Search
CPC ............................ G01N 23/046; G01V 5/0016
USPC ....................................................... 250/395
See application file for complete search history.

(56) References Cited

U.S. PATENT DOCUMENTS

| | | |
|---|---|---|
| 5,528,703 A | 6/1996 | Lee |
| 8,019,556 B2 | 9/2011 | Shpantzer et al. |
| 8,247,767 B2 | 8/2012 | Morris et al. |
| 2004/0114800 A1* | 6/2004 | Ponomarev ........... G06T 7/0012 382/173 |
| 2008/0128604 A1 | 6/2008 | Bryman |
| 2008/0315091 A1* | 12/2008 | Morris ...................... G01T 1/18 250/307 |

(Continued)

OTHER PUBLICATIONS

Borozdin, K. N., et al., "Surveillance: Radiographic Imaging with Cosmic Ray Muons," Nature, 422:277-278, Mar. 2003.

(Continued)

*Primary Examiner* — David Porta
*Assistant Examiner* — Abra Fein
(74) *Attorney, Agent, or Firm* — Perkins Coie LLP

(57) ABSTRACT

Techniques, systems, and devices are disclosed for analyzing a point of closest approach (PoCA) image of a volume of interest (VOI) comprising a set of recorded PoCA points from charged particle detector measurements to detect an object within the VOI. The VOI is partitioned into a set of equally-sized bins with each bin including a subset of the PoCA points. A bin metric is determined for each bin. A subset of the bins is selected based on the detected bin metric with the subset of bins being most likely to contain objects. A potential object for each selected bin is determined by determining a location and a size for the potential object based at least on the PoCAs inside the bin. A figure of merit (FOM) of the potential object is determined as a measure of the likelihood that the potential object is truly a threat object.

32 Claims, 11 Drawing Sheets

(56) References Cited

U.S. PATENT DOCUMENTS

| | | |
|---|---|---|
| 2010/0065745 A1 | 3/2010 | Goldberg et al. |
| 2014/0322685 A1* | 10/2014 | Kennerly ............... G09B 19/00 434/236 |
| 2015/0212014 A1 | 7/2015 | Sossong et al. |
| 2016/0097729 A1 | 4/2016 | Kurnadi et al. |

OTHER PUBLICATIONS

International Search Report and Written Opinion dated Nov. 24, 2015 for International Application No. PCT/US2015/047598, filed on Aug. 28, 2015 (9 pages).

\* cited by examiner (10 sec to 80 sec)

(90 sec to 120 sec)

DETECTION OF AN OBJECT WITHIN A VOLUME OF INTEREST

CROSS REFERENCE TO RELATED APPLICATIONS

This patent document timely claims the priority and benefits of U.S. Provisional Patent Application No. 62/043,323, filed on Aug. 28, 2014. The entire content of the before-mentioned patent application is incorporated by reference as part of the disclosure of this document.

TECHNICAL FIELD

The subject matter described in this disclosure generally relates to systems, devices, and processes for inspecting objects (e.g., cargos or containers) and volumes for detecting certain substances or items e.g., prohibited items including explosives, weapons, and nuclear materials.

BACKGROUND

Cosmic ray imaging and sensing are techniques that exploit the multiple Coulomb scattering of highly penetrating cosmic ray-produced muons to perform non-destructive inspection of materials without the use of artificial radiation. The Earth is continuously bombarded by energetic stable particles, mostly protons, coming from deep space. These particles interact with atoms in the upper atmosphere to produce showers of particles that include many short-lived pions, which decay into longer-lived muons. Muons interact with matter primarily through the Coulomb force, having no nuclear interaction and radiating much less readily than electrons. Such cosmic ray-produced particles slowly lose energy through electromagnetic interactions. Consequently, many of the cosmic ray produced muons arrive at the Earth's surface as highly penetrating charged radiation. The muon flux at sea level is about 1 muon per cm$^2$ per minute.

As a muon moves through material, Coulomb scattering off of the charges of sub-atomic particles perturb its trajectory. The total deflection depends on several material properties, but the dominant effects are the atomic number, Z, of nuclei and the density of the material. The trajectories of muons are more strongly affected by materials that make good gamma ray shielding, such as lead and tungsten, and by special nuclear materials (SNM), such as uranium and plutonium, than by materials that make up more ordinary objects such as water, plastic, aluminum and steel. Each muon carries information about the objects that it has penetrated. The scattering of multiple muons can be measured and processed to probe the properties of these objects. A material with a high atomic number Z and a high density can be detected and identified when the material is located inside low-Z and medium-Z matter. In addition to muons, cosmic rays also generate electrons. Electrons are less massive and generally have lower momenta than muons and hence scatter more in a given material. Due to their larger scattering, electrons can be used to differentiate materials particularly those with low to medium Z and densities that may not significantly scatter muons.

Coulomb scattering from atomic nuclei in matter results in a very large number of small angle deflections of charged particles as they transit the matter. In some examples, a correlated distribution function can be used to approximately characterize the displacement and angle change of the trajectory that depends on the density and the atomic charge of the material. As an example, this distribution function can be approximated as a Gaussian distribution. The width of the distribution function is proportional to the inverse of the momentum of the particle and the square root of the real density of material measured in radiation lengths. The correlated distribution function of cosmic ray-produced particles (e.g., muons and electrons) can provide information on materials in the paths of the particles with no radiation dose above the Earth's background and proper detection of such cosmic ray-produced particles can be implemented in a way that is especially sensitive to selected materials to be detected such as good radiation shielding materials.

In some examples of cosmic ray imaging and sensing, a muon tomography system can be configured to perform tomography of a target object under inspection based on scattering of cosmic ray particles by the target object. For example, cosmic ray tomography systems can be used for detecting certain targeted objects, e.g., such as materials that can be used to threaten the public, including smuggled nuclear materials. Cosmic ray tomography detector systems can be used jointly with or an alternative to other nuclear material detectors such as gamma or X-ray detectors. Gamma and X-ray detectors operate by directing Gamma and X-ray radiation to a target and measuring penetrated Gamma and X-ray radiation. Shielding of nuclear materials can reduce the count rates in the Gamma and X-ray detectors and reduce the detection performance of Gamma and X-ray detectors. Cosmic ray tomography detection systems can be configured to detect shielded nuclear materials and objects.

In an example of a cosmic ray tomography detection system, the cosmic ray particle detectors can include arrays of drift-tube sensors configured to enable tomographic imaging of a volume of interest (VOI) using ambient cosmic rays as the illuminating radiation source. Cosmic ray charged particles, e.g., primarily muons and electrons, shower through the VOI, and measurement of individual particle tracks can be used to reconstruct the three-dimensional distribution of atomic number (Z) and density of materials in the VOI using particle scattering.

SUMMARY

Disclosed are techniques, systems, and devices for analyzing a content of a volume, such as a cargo or container, based on direct detector measurements (i.e., charged cosmic ray particles tracks as charged cosmic ray particles passing through the volume), images obtained from cosmic ray particle detector measurements, or a combination of direct detector measurements and charged particle images to detect certain targeted substances or objects/items that are present inside the volume or object under inspection. In some techniques, particle tracks entering and exiting the VOI are paired and evaluated to locate the point closest to a single effective scattering site (referred to as the point of closest approach or "PoCA"). At the same time, the effective scattering angle is calculated. The probability of scattering and the size of the scattering angle are both generally directly related to the atomic mass of the scattering atom. Thus, a greater density of scattering centers and/or a greater average scattering angle tend to indicate the presence of high atomic mass material such as SNM.

In one aspect, a technique for analyzing a point of closest approach (PoCA) image of a volume of interest (VOI) including a set of recorded PoCA points from charged particle detector measurements to detect one or more objects within the volume is disclosed. The VOI can be partitioned into a set of equally-sized bins with each bin including a subset of PoCA points in the set of PoCA points. For each bin in the set of bins, a bin metric can be determined. In one embodiment, determining the bin metric can include determining a median effective scattering angle for each bin in the set of bins. A subset of bins in the set of bins can be selected based on the determined bin metric, with the selected subset of bins being most likely to contain objects. A potential object for each of the selected subset of bins can be identified by determining a location and a size for the potential object based at least on the PoCAs inside the corresponding bin. After identifying a potential object, a figure of merit (FOM) of the potential object can be determined as a measure of the likelihood that the potential object is truly a target object, such as a threatening object.

In some implementations, selecting the subset of bins in the set of bins can include selecting the top N bins in the set of bins with the highest product between the numbers of scattered charged particles and the computed median effective scattering angle. The subset of bins are non-adjacent bins. Furthermore, N is a user-selected number chosen to be large compared to the number of separate objects that are expected in the VOI, wherein the number of separate objects includes threatening objects, non-threatening objects of interest, and other non-threatening objects.

In another aspect, a system is disclosed for using cosmic ray-generated charged particles to inspect objects in an object holding area. This system includes a first set of position sensitive particle detectors located on a first side of an object holding area to measure positions and directions of incident charged particles towards the object holding area that are caused cosmic rays; a second set of position sensitive particle detectors located on a second side of the object holding area opposite to the first side to measure positions and directions of outgoing charged particles exiting the object holding area; and a signal processing unit to receive data of measured signals of the incident charged particles from the first set of position sensitive particle detectors and measured signals of the outgoing charged particle from the second set of position sensitive particle detectors, the signal processing unit is configured to analyze scattering behaviors of the charged particles caused by scattering of the charged particles within the object holding area based on the measured incoming and outgoing positions and directions of the charged particle to construct a point of closest approach (PoCA) image of a volume of interest (VOI) within the object holding area comprising a set of recorded PoCA points from the received data. The signal processing unit is configured to analyze the PoCA image to detect one or more objects within the VOI and performs:partitioning the VOI into a set of bins wherein each bin includes a subset of PoCA points in the set of PoCA points; determining a bin metric for each bin in the set of bins; selecting a subset of bins in the set of bins based on the determined bin metric, wherein the subset of bins is most likely to contain objects; and determining a potential object for each of the selected subset of bins by determining a location and a size for the potential object based at least on the PoCAs inside the bin.

The above and other aspects of the disclosed technology and various implementations and examples are described in greater detail in the drawings, the description and the claims.

DETAILED DESCRIPTION

Figure 1:
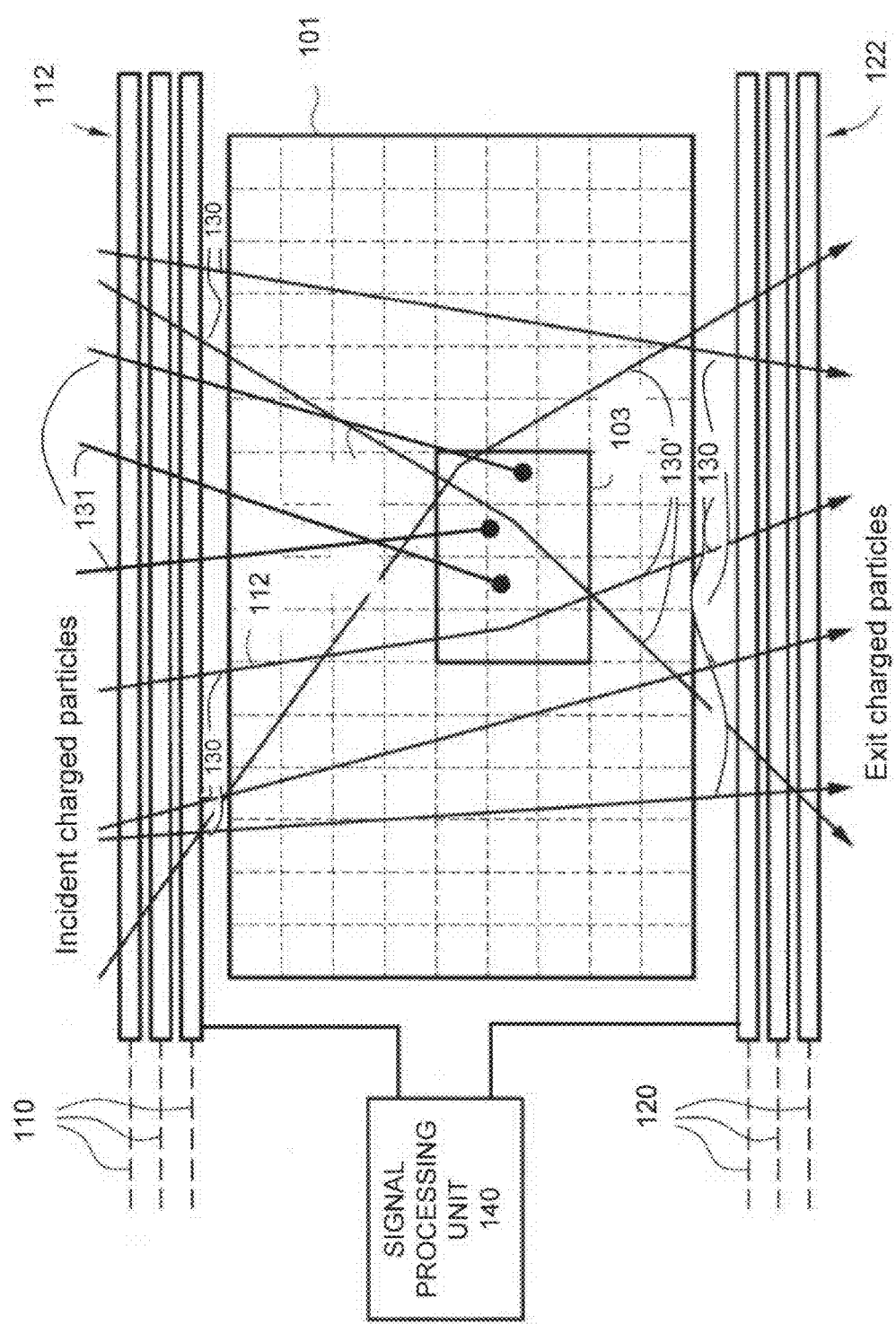
FIG. 1 shows an exemplary cosmic-ray particle tomography system in accordance with some embodiments described herein.

A tomography system can be configured based on cosmic ray imaging and sensing to obtain tomographic information of a target volume or object under inspection based on scattering of the charged particles by the target volume or object. For example, muon tomography systems can be used for detecting certain targeted objects, e.g., such as materials that can be used to threaten the public, including smuggled nuclear materials. Cosmic ray tomography detector systems can be used jointly with or an alternative to other nuclear material detectors such as gamma or X-ray detectors. Gamma and X-ray detectors operate by directing Gamma and X-ray radiation to a target and measuring penetrated Gamma and X-ray radiation. Shielding of nuclear materials can reduce the count rates in the Gamma and X-ray detectors and reduce the detection performance of Gamma and X-ray detectors. Cosmic ray tomography detection systems can be implemented to detect shielded nuclear materials and objects.

In an example of a muon tomography detection system, muon detectors can include arrays of drift-tube sensors implemented to enable tomographic imaging of a volume of interest (VOI) using the naturally occurring charged particles from cosmic rays as the illuminating radiation source. Cosmic ray charged particles, e.g., primarily muons and electrons, shower through the VOI, and measurement of individual particle tracks can be used to reconstruct the three-dimensional distribution of the atomic number (Z) and density of materials in the VOI using particle scattering.

Disclosed are techniques, systems, and devices for analyzing contents of a volume, such as a cargo or container, based on direct detector measurements (i.e., charged cosmic ray particles tracks as charged cosmic ray particles passing through the volume), images obtained from cosmic ray particle detector measurements, or a combination of direct detector measurements and charged particle images, to detect certain targeted substances or objects/items that are present inside the volume or object under inspection. In some techniques, particle tracks entering and exiting the VOI are paired and evaluated to locate the point closest to a single effective scattering site (referred to as the point of closest approach or "PoCA"). At the same time, the effective scattering angle is calculated. The probability of scattering and the size of the scattering angle are both generally directly related to the atomic mass of the scattering atom. Thus, a greater density of scattering centers and/or a greater average scattering angle tend to indicate the presence of a high atomic mass material, e.g., a special nuclear material (SNM) such as a uranium material or other materials of interest for inspection.

In one aspect, a technique is described for analyzing a raw point of closest approach (PoCA) image of a volume of interest (VOI) including a set of recorded PoCA points from charged particle detector measurements to detect one or more objects within the volume. The VOI is partitioned into a set of equally-sized bins with each bin including a subset of PoCA points in the set of PoCA points. A bin metric is determined for each bin in the set of bins. In one embodiment, determining the bin metric includes determining a median effective scattering angle for each bin in the set of bins. A subset of bins in the set of bins is selected based at least on the computed bin metric, with the selected subset of bins being most likely to contain objects. A potential object for each of the selected subset of bins can be identified by determining a location and a size for the potential object based at least on the PoCAs inside the bin. After identifying a potential object, a figure of merit (FOM) of the potential object can be determined as a measure of the likelihood that the potential object is truly a target object, such as a threatening object.

The cosmic-ray particle detection systems, devices and techniques described in this patent document can be implemented to detect the presence of certain objects or materials such as nuclear materials. Tomographic information of such objects can be obtained in various applications including but not limited to inspecting packages, containers, occupied vehicles at security check points, border crossings and other locations for nuclear threat objects that may range from fully assembled nuclear weapons to small quantities of highly shielded nuclear materials. The described systems, devices and techniques can be used to construct or supplement various particle detection systems to meet specific detection or inspection needs.

For example, a particle detection system can include an object holding area for placing an object to be inspected, a first set of position sensitive cosmic-ray particle detectors located on a first side of the object holding area to measure positions and directions of incident cosmic-ray particle towards the object holding area, a second set of position sensitive cosmic-ray particle detectors located on a second side of the object holding area opposite to the first side to measure positions and directions of outgoing cosmic-ray particle exiting the object holding area, and a signal processing unit, which may include, e.g., a microprocessor, to receive data of measured signals of the incoming charged particles from the first set of position sensitive cosmic-ray particle detectors and measured signals of the outgoing cosmic-ray particle from the second set of position sensitive particle detectors. As an example, each of the first and second sets of particle detectors can be implemented to include drift tubes arranged to allow at least three charged particle positional measurements in a first direction and at least three charged particle positional measurements in a second direction different from the first direction. The signal processing unit is configured to analyze scattering behaviors of the cosmic-ray particles caused by scattering of the cosmic-ray particles in the materials within the object holding area based on the measured incoming and outgoing positions and directions of cosmic-ray particle to obtain a tomographic profile or the spatial distribution of scattering centers within the object holding area.

The obtained tomographic profile or the spatial distribution of scattering centers can be used to reveal the presence or absence of one or more objects in the object holding area such as materials with high atomic numbers, including nuclear materials or devices. Each position sensitive particle detector can be implemented in various configurations, including drift cells such as drift tubes filled with a gas that can be ionized by charged particles. Such a system can be used to utilize naturally occurring cosmic-ray particles as the particle source for detecting one or more objects in the object holding area.

In applications for portal monitoring, the illustrative embodiments provide an approach to robust nuclear material detection at a reduced cost and with increased effectiveness in comparison with other detection systems. The disclosed technology can provide a radiation portal monitor that is capable of determining whether a given vehicle or cargo is free of nuclear threats by both measuring the absence or presence of a potential shielded package and measuring the absence or presence of a radiation signature.

The portal monitoring systems of the illustrative embodiments shown in the accompanying drawings employ cosmic ray-produced charged particle tracking with drift tubes. As will be explained in more detail below, the portal monitoring systems utilize drift tubes to enable tracking of charged particles, such as muons and electrons, passing through a volume as well as detection of gamma rays. Advantageously, these portal monitoring systems can effectively provide the combined function of a cosmic ray radiography apparatus with passive or active gamma radiation counter to provide a robust detector for nuclear threats. The combined detection of muons and gamma rays can eliminate the need for two separate instruments. Cosmic ray tomography is a technique that exploits the multiple Coulomb scattering of highly penetrating cosmic ray-produced muons to perform non-destructive inspection of the material without the use of artificial radiation.

As a muon moves through a material, Coulomb scattering off of the charges of sub-atomic particles perturb its trajectory. The total deflection depends on several material properties, but the dominant effect is the atomic number, Z, of nuclei. The trajectories are more strongly affected by materials that make good gamma ray shielding (such as lead and tungsten for example) and by special nuclear material (SNM), that is, uranium and plutonium, than by materials that make up more ordinary objects such as water, plastic, aluminum and steel. Each muon carries information about the objects that it has penetrated, and by measuring the scattering of multiple muons one can probe the properties of these objects. A material with a high atomic number Z and a high density can be detected and identified when the material is located inside low-Z and medium-Z matter.

Coulomb scattering from atomic nuclei results in a very large number of small angle deflections of charged particles as they transit the matter. The result is a correlated Gaussian distribution function for the displacement and angle change of the trajectory that depends on the density and the atomic charge of the material. The width of the distribution function is proportional to the inverse of the momentum of the particle and the square root of the real density of material measured in radiation lengths. Further background can be found in the reference of K. N Borozdin et al. entitled "Surveillance: Radiographic Imaging with Cosmic Ray Muons", published in Nature (2003), 422, 277.

Cosmic ray-produced muons and electrons can provide information with no radiation dose above the earth's background and proper detection of such cosmic ray-produced muons and electrons can be implemented in a way that is especially sensitive to good shielding materials. A detection system can be configured to perform tomography of a target object under inspection based on scattering of muons and electrons by the target object. The system can be configured to perform tomography to localize scattering. The tomographic position resolution can be expressed approximately as follows:

$$\Delta x = \theta_{RMS} L$$

where:

$\theta_{RMS}$=the root-mean-square (rms) of the scattering angle, and

L=the size of the volume under the detection by the detection apparatus.

For example, for an exemplary rms scattering angle of 0.02 radian and an apparatus size of 200 cm, the tomographic position resolution is 0.02×200 cm=4 cm.

In one approach, the angular resolution is determined by the following equation based on the Poisson statistics:

$$\frac{\Delta \theta}{\theta} = \frac{1}{\sqrt{2N}}$$

where θ is the root mean square (rms) value of the scattering angle, and N is the number of cosmic ray-produced muons and/or electrons passing through a region of interest. For example, the angular resolution for N=100 (corresponding to a 10×10 cm² resolution element after one minute of counting) is Δθ=0.078.

Tomographic methods, designed to construct an image or model of an object from multiple projections taken from different directions, can be implemented in the cosmic ray system to provide a discrete tomographic reconstruction of the volume of interest based on the data provided by the cosmic-ray particles. In some implementations, Monte Carlo simulation techniques can be used to study applications and shorten scanning times. Other stochastic processing methods may also be used in implementing the cosmic ray tomographic imaging described in this application.

The cosmic ray radiography function of the particle detection systems of the embodiments can be more readily understood with reference to examples of detection systems adapted to detect cosmic ray-produced charged particles such as those shown in FIG. 1. Referring initially to FIG. 1, which illustrates an exemplary detection system utilizing cosmic-ray particles to detect an object, system 100 includes a set of two or more planes 110 of incoming charged particle detectors 112 arranged above a volume 101 to be imaged as the first array of detectors for providing the position and angles (i.e., directions in the 3-D space) of incoming charged particle tracks 130 and 131. The incoming charged particle detectors 112 are implemented to measure the position and angles of incoming charged particle tracks 130 and 131 with respect to two different directions, e.g., in two orthogonal coordinates along x and y axes. Charged particles (e.g., muons and electrons) pass through the volume 101 where the VOI 103 may be located and are scattered to an extent dependent upon the material occupying the volume 103 through which they pass. Another set of two or more planes 120 of outgoing charged particle detectors 122 are implemented as the second array of detectors to record outgoing charged particle positions and directions. The drift tubes in detectors 112 and 122 are arranged to allow at least three charged particle positional measurements in a first direction and at least three charged particle positional measurements in a second direction which is different from the first direction and may be orthogonal to the first direction. Side detectors (not shown) may be used to detect more horizontally orientated muon tracks. The scattering angle of each charged particle is computed from the incoming and outgoing measurements.

A signal processing unit 140, e.g., a computer, is provided in the system 100 to receive data of measured signals of the incoming charged particles by the detectors 112 and outgoing charged particles by the detectors 122. This signal processing unit 140 is configured to analyze the scattering of the charged particles in the volume 101 based on the measured incoming and outgoing positions and directions of charged particles to obtain a tomographic profile or the spatial distribution of the scattering density reflecting the scattering strength or radiation length within the volume 101. The obtained tomographic profile or the spatial distribution of the scattering density within the volume 101 can reveal the content of the VOI 103 in the volume 101. FIG. 1 shows drift tube detectors 112 and 122 located on top and bottom sides of the volume 101. In some implementations, additional drift tube detectors can be implemented on sides of the volume 101 to form a box or four sided structure into which a package, a vehicle or cargo container can enter for scanning by the system.

The processing of measurements for cosmic ray particles in a volume under inspection (e.g., a package, a container or a vehicle) by the signal processing unit 140 for the system 100 in FIG. 1, and other systems described in this application can include reconstructing the trajectory of a charged particle such as a muon or an electron through the volume 101, measuring the momentum of an incoming charged particle based on signals from the detectors 112, measuring the momentum of an outgoing charged particle based on signals from the detectors 122, and determining the spatial distribution of the scattering density of the volume 101. These and other processing results can be used to construct the tomographic profile and measure various properties of the volume 101.

For example, the reconstruction of the trajectory of a charged particle passing through a detector having a set of drift cells can include (a) obtaining hit signals representing identifiers of drift cells hit by charged particles and corresponding hit times; (b) grouping in-time drift cell hits identified as being associated with a track of a particular charged particle passing through the detector; (c) initially estimating a time zero value for a moment of time at which the particular charged particle hits a drift cell; (d) determining drift radii based on estimates of the time zero values, drift time conversion data and the time of the hit; (e) fitting linear tracks to drift radii corresponding to a particular time zero value; and (f) searching and selecting a time-zero value associated with the best of the track fits performed for a particular charged particle and computing error in time-zero and tracking parameter. Reconstruction of the track based on the time zero fit provides a reconstructed linear trajectory of the charged particle passing through the charged particle detector without having to use fast detectors (such as photomultiplier tubes with scintillator paddles) or some other fast detector that detects the passage of the muon through the apparatus to the nearest few nanoseconds to provide the time-zero.

Also for example, measuring the momentum of an incoming or outgoing charged particle based on signals from the detectors can include, for example, (a) configuring multiple position sensitive detectors to scatter a charged particle passing through the position sensitive detectors; (b) measuring the scattering of a charged particle in the position sensitive detectors including obtaining at least three positional measurements of the scattering charged particle; (c) determining at least one trajectory of the charged particle from the positional measurements; and (d) determining at least one momentum measurement of the charged particle from the at least one trajectory. The momentum of the charged particle can be determined based on the trajectory of the charged particle, which is determined from the scattering of the charged particle in the position sensitive detectors themselves without the use of additional metal plates in the detector.

Also for example, the spatial distribution of the scattering density of the volume can be determined from charged particle tomographic data by: (a) obtaining predetermined charged particle tomography data corresponding to scattering angles and estimated momentum of charged particles passing through object volume; (b) providing the probability distribution of charged particle scattering for use in an image reconstruction technique such as an expectation maximization (ML/EM) technique, the probability distribution being based on a statistical multiple scattering model; (c) determining an estimate of the object volume density, e.g., by determining a substantially maximum likelihood estimate using the expectation maximization (ML/EM) technique; and (d) outputting reconstructed object volume scattering density. The reconstructed object volume scattering density can be used to identify the presence and/or type of object occupying the volume of interest from the reconstructed volume density profile. Various applications include cosmic ray particles tomography for various homeland security inspection applications in which vehicles or cargo can be scanned by a charged particle tracker.

The tomographic processing part of the signal processing unit 140 may be implemented in a computer at the same location as the detectors 112 and 122. Alternatively, the tomographic processing part of the signal processing unit 140 may be implemented in a remote computer that is connected on a computer network such as a private network or a public network such as the Internet.

Further referring to FIG. 1, incoming charged particle detectors 112 can detect the X-Y position, angle, speed, and momentum of each of the incident charged particles 130 and 131 entering the volume 101, while outgoing charged particle detectors 122 can detect the X-Y position, angle, speed, and momentum of each of the exiting charged particles 130 passing through volume 101. The signal processing unit 140 is configured to process the position, angle, speed, and momentum data collected by detectors 112 and detectors 122 to match each incident charged particle 130 with a corresponding exiting charged particle 130. The signal processing unit 140 is also configured to process the position, angle, speed, and momentum data collected by detectors 112 and detectors 122 to identify those exiting charged particles 130 that are scattered by VOI 103, such as charged particles 130', and generate a scattering number for the incident charged particles. The signal processing unit 140 is also configured to process the position, angle, speed, and momentum data collected by detectors 112 and detectors 122 to identify incident charged particles 131 which are stopped inside VOI 103 and generate a stopping number for the incident charged particles.

Further detail of cosmic-ray particle tomography systems which can be used to detect and identify content of a VOI exposed to cosmic ray particles based on the measured scattering and stopping characteristics of the cosmic ray particles is described in U.S. Pat. No. 8,247,767 entitled "PARTICLE DETECTION AND APPLICATIONS IN SECURITY AND PORTAL MONITORING" filed on Oct. 26, 2007, the content of which is incorporated by reference as part of the specification of this application.

Tomography of a volume of interest (VOI) using ambient cosmic-ray radiation yields approximate locations of cosmic-ray particle (mainly muon and electron) scattering events, along with estimates of the scattering angle, throughout the VOI. Both the density and angle of scattering events are generally proportional to the density and atomic number of the material inside the VOI. After the reconstruction of the locations and angles of scattering events, the reconstructed cosmic-ray charged particle image ("charged particle image" hereinafter) can be analyzed to determine the location and size of object of interest (e.g., special nuclear materials or "SNM"). Because more than one object of interest may be located within the VOI, object identification and characterization operations should be robust to ensure reliable detections of object of interest with minimal false alarms.

The techniques, systems and devices described in the present disclosure can be used to provide robust identifications of the number of objects, the associated sizes, and the associated atomic numbers. The described techniques, systems and device do not rely on unsophisticated thresholds to identify objects. In addition, the described techniques, systems and devices are optimized to detect multiple objects within a VOI, and can potentially eliminate missed detections and false alarms.

Particle tracks entering and exiting the VOI can be paired and evaluated to locate the point closest to a single effective scattering site (referred to as the point of closest approach or "PoCA"). While locating the PoCA, the effective scattering angle can be determined at the same time or at least partially concurrently. The probability of scattering and the size of the scattering angle are both generally directly related to the atomic mass of the scattering atom. Thus, a greater density of scattering centers and/or a greater average scattering angle tend to indicate the presence of high atomic mass material such as SNM.

Mitigating Bin Edge Effects

In one implementation, a reconstructed charged particle image of a VOI is divided into voxels or bins (consistently referred to as "bins" hereinafter) for object identification, and bins with more scattering sites are identified as more likely to contain high atomic mass material (hereinafter referred to as an "object", as in an object of potential interest). Generally, scattering sites belong to an object fall into a given bin. However, in some occasions, a dense object may be split between two adjacent bins (or even more bins if the objects falls near a corner of a given bin). In such cases, the computed density of scatterers is also split between bins, which can often cause missing detection of an object.

To mitigate this problem, one embodiment of the present technique shifts each bin by ±½ of the linear dimension of the bin along each of the three axes x, y and z. This operation generates 27 possible bin positions (i.e., 1 unshifted position and 26 shifted positions).

Figure 2:
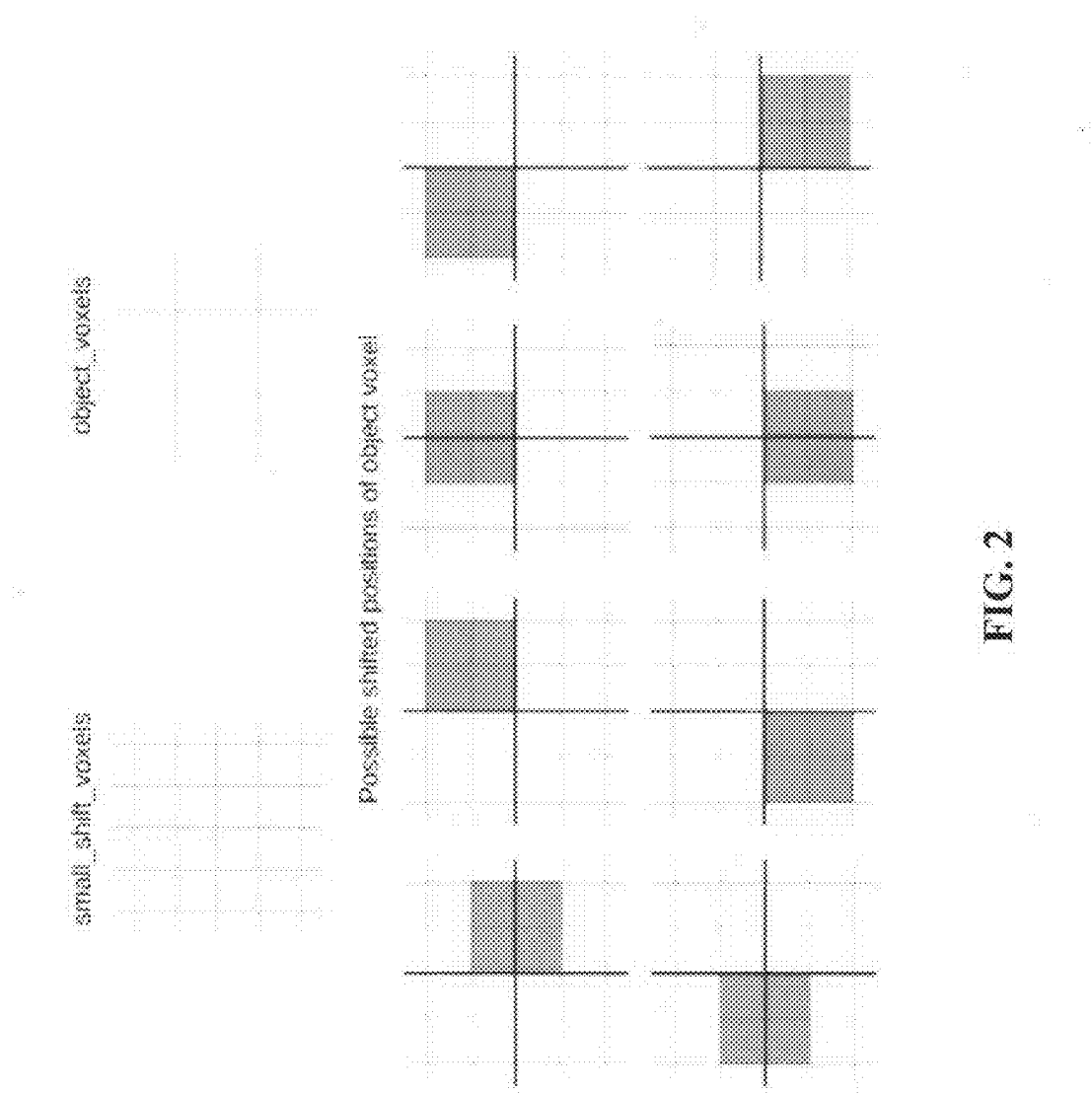
FIG. 2 illustrates an example process of generating different bin positions by shifting a bin in two dimensions by ±½ of the bin dimension.

FIG. 2 illustrates an example process of generating different bin positions by shifting a bin in two dimensions (the unshifted bin is not shown) by ±½ of the bin dimension, which creates eight shifted positions of a bin in two dimensions (unshifted position not shown). In one embodiment, the half bin shift is implemented by binning the particle track PoCAs into temporary smaller bins, each of ½ the width (in all three dimensions) of the standard object bin. After generating the shifted bin positions, for each bin position, the median scattering angle of particle tracks with PoCAs falling into that bin position is computed. The highest of the 27 median scattering angle values is then assigned to the unshifted bin. In this manner, the bin edge effect on the object detection can be effectively mitigated.

Detection of Multiple Objects in a VOI

Figure 3:
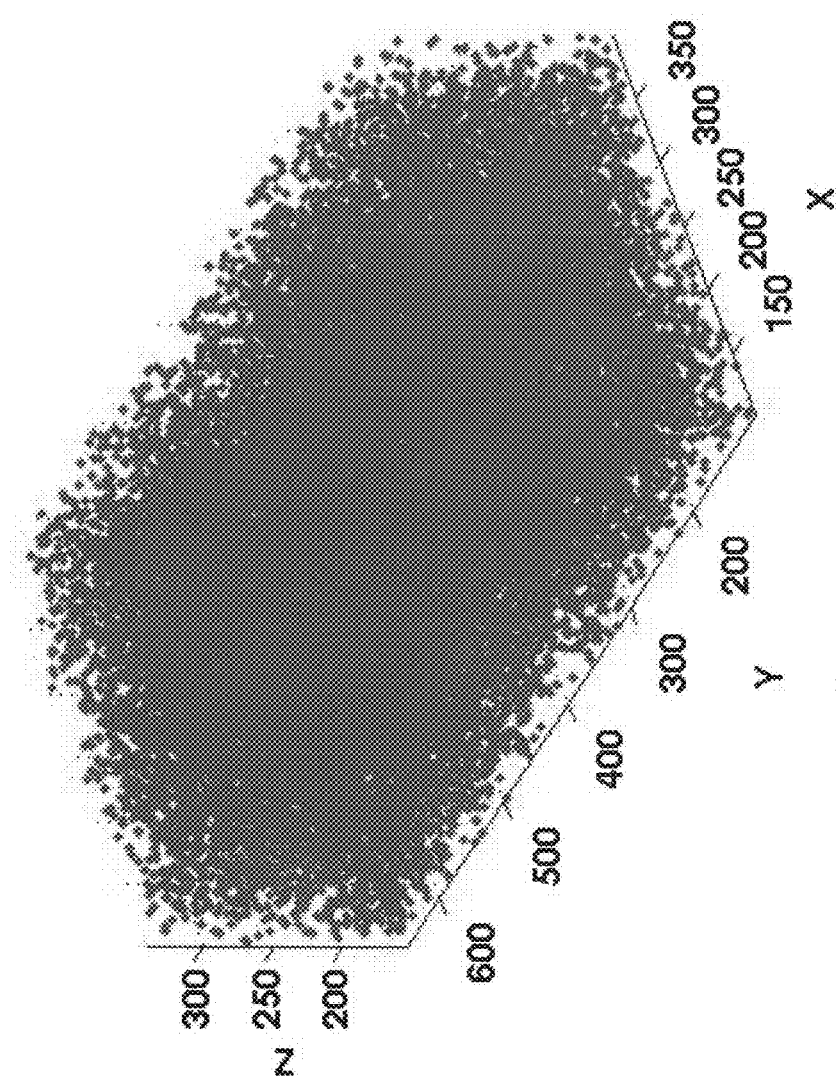
FIG. 3 illustrates an exemplary tomography image of a VOI showing locations of PoCA points in bins inside the VOI.

FIG. 3 illustrates an exemplary tomography image of a VOI showing locations of PoCA points (also referred to as "PoCAs") in bins inside the VOI. In one embodiment, PoCA points are obtained based on charged particle tracks, such as muon tracks. As can be seen in FIG. 3, it is difficult to visually identify objects based on the raw PoCA points. In one embodiment, to identify objects of interest based on the identified PoCA points, a proper bin size is first determined. In one embodiment, the bin size is selected according to the number of particle tracks, or the number of PoCAs inside the VOI. For example, the bin size may be determined such that there are on average 10 PoCAs per bin. However, in other embodiments, there can be greater or fewer than 10 PoCAs per bin for bin size selection. In one embodiment, the number of PoCAs per bin can be sufficiently large to avoid computational instability. On the other hand, when the number of PoCAs is too large, the bin size becomes too large for identifying smaller objects. When the number of PoCAs per bin is fixed, the bin size becomes a time-varying parameter. At an earlier time, the bin size is relatively large because the number of observed particle tracks is small. Note that a bin of such a large bin size may contain multiple objects. However, as the observation time increases, the bin size can be reduced smaller as more and more particle tracks are recorded, thus improving the spatial resolution of the obtained image.

Once the PoCAs are assigned into bins, the bin-shifting process is applied to determine the median effective scattering angle for each bin. In one embodiment, the median effective scattering angle for each bin is determined using a maximum likelihood estimate, assuming that the scattering angles are distributed according to a log-normal distribution. Hence, the mean of the logarithm of the scattering angles yields the median scattering angle under this assumption. In practice, the scattering angle is actually determined as the product of the particle momentum and the associated scattering angle. The product quantity is assumed to be log-normally distributed, and the median of the quantity is used as the median effective scattering angle.

As a part of the object identification process, the top N non-adjacent bins are chosen. In choosing the top N non-adjacent bins, the top N non-adjacent bins can be selected with the highest product between the numbers of scattered muons and the median effective scattering angle, where N is a user-selected number chosen to be large compared to the number of separate objects that may be expected in the VOI. In one embodiment, the number of separate objects includes threatening objects, such as weapons, explosives and nuclear materials, non-threatening objects of interest, such as drugs, tobaccos, and precious metals, and other non-threatening objects. (Threatening objects and non-threatening objects of interest are collectively referred to as "target objects.") For example, N is chosen to be 1000 in some implementations. In an alternative embodiment, the top N bins with the highest product between the numbers of scattered muons and the median effective scattering angle, which can include adjacent bins, are selected.

Also, the Center of Mass (CM) of each of the selected bin, which is considered as a potential object, is determined based on the momenta $p_i$ and scattering angles $\theta_i$ associated with the PoCAs inside the selected bin and those of surrounding bins:

$$CM=(\Sigma p_i \theta_i {}^* x_i)/(\Sigma p_i \theta_i),$$

where $x_i$ represents the position of the ith PoCA. In one embodiment, the PoCAs included in the above equation's summation are the ones that fall within a volume that is twice the widths of the bin and is centered on the bin. In this embodiment, because the volume extends to about half-way into the neighboring bins, the PoCAs includes both those in the selected bin, and some of the PoCAs inside each of (up to) 26 neighboring bins.

After computing the CM, the selected bin is re-centered to the location of the associated CM location as determined above, the bin metric such as the median effective scattering angle is recomputed. The process is repeated for each of the N top bins to locate the CM of each potential object.

Estimating the Volume and Figure of Merit of a Potential Object

Figure 4:
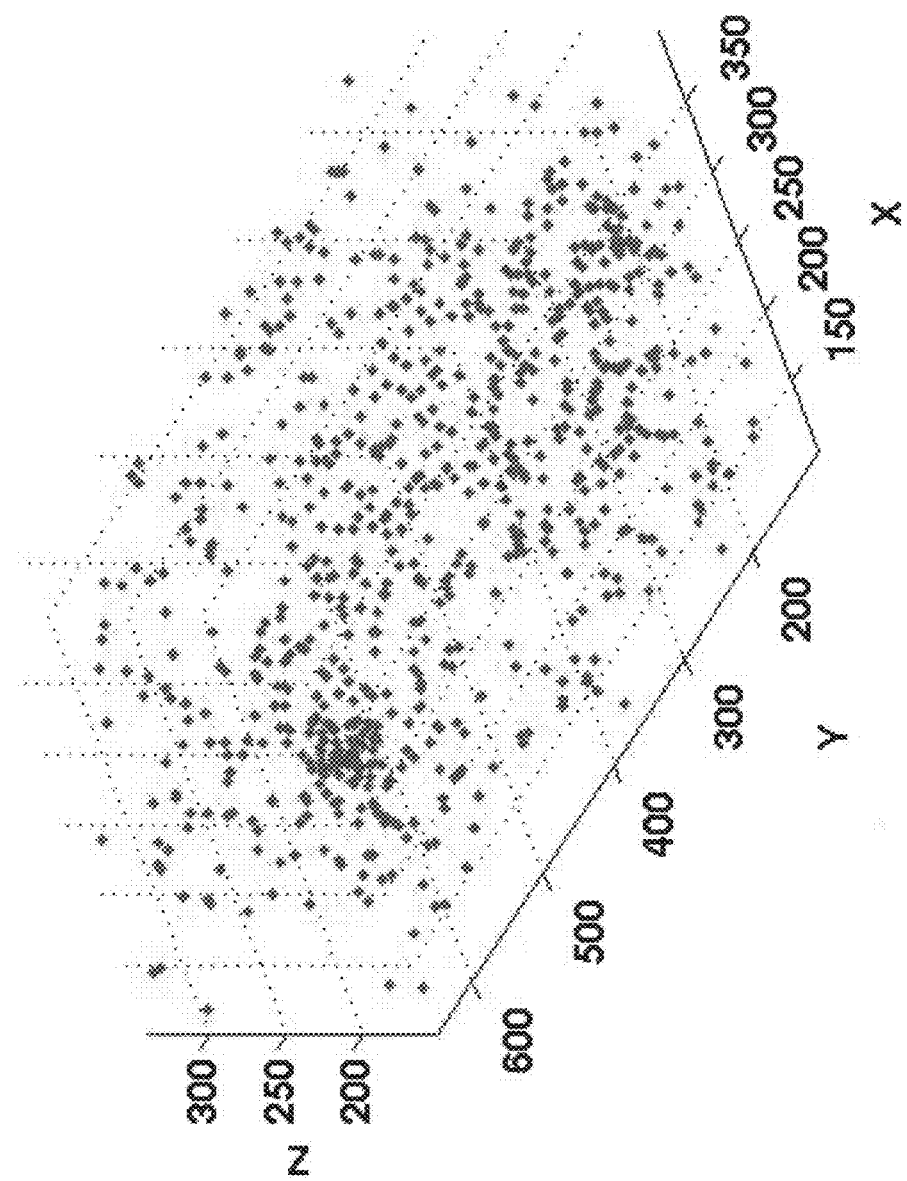
FIG. 4 illustrates the exemplary result of filtering the raw data of FIG. 3 by selecting the PoCAs falling in the highest 1% of the expected distribution constructed based on the raw PoCAs data in FIG. 3.

Prior to estimating the volume of a potential object, the raw PoCA data set may be preprocessed to remove low value points (i.e., background noise) to emphasize PoCAs that correspond to scattering due to high atomic number material. In one embodiment, a $(p\theta)$ cutoff point is selected that is then used to filter the raw PoCA points within each of the N selected bins for background noise rejection. For example, PoCAs corresponding to scatterings in normal objects are considered as background noise, which are targets for filtering. One way to obtain the $(p\theta)$ cutoff is based on using the log-normal distribution assumption of $(p\theta)$ as described above. The log-normal distribution of $(p\theta)$ is constructed by computing the geometric mean and geometric standard deviation of the log-normally distributed $(p\theta)$. In one embodiment, the geometric mean is determined using the raw data set of PoCA points, for example, the raw data in PoCA image of FIG. 2. Note that the current mean and standard deviation of the normally distributed $\ln(p\theta)$ are substantially equivalent to the geometric mean and geometric standard deviation of $(p\theta)$. Once the PoCA distribution has been constructed, a $(p\theta)$ cutoff point may be determined to achieve a user-specified constant false alarm rate (CFAR). A given CFAR corresponds to a percentage value of the expected distribution, wherein PoCA points distributed below this percentage value can be eliminated. For example, FIG. 4 illustrates the exemplary result of filtering the raw data of FIG. 3 by selecting the PoCAs falling above the cutoff value corresponding to the highest 1% of the expected distribution constructed based on the raw PoCAs data in FIG. 3.

After data filtering, a bin metric defined as the product of the median scattering angle and the number of muons in a given bin, can be computed for each selected bin. Recall that the higher the density and atomic number of the material in a given bin, the greater the number of scattered muons and the larger the median scattering angle. The bin metric thus strongly indicates the likely density and atomic number of a bin.

In one embodiment, the object size of a selected bin can be obtained based on a PoCA histogram of the bin metric values. After filtering the raw PoCAs data, adjacent bins have different numbers of scattered charged particles, such as muons. The object size can be determined independently in each dimension, x, y or z. To build a histogram in a given direction x, y or z, a set of equal sized histogram bins is defined along that direction which is centered around the determined CM in that direction. Next, for each histogram bin, a charged particle frequency is determined, which may be determined as the number of PoCAs within the histogram bin divided by the total PoCAs in the potential object (i.e., the selected bin). In one embodiment, the PoCAs used in histogram calculation include exclusively the PoCAs retained after performing the CFAR filtering, rejecting those PoCAs with pθ less than the cutoff value.

Figure 5:
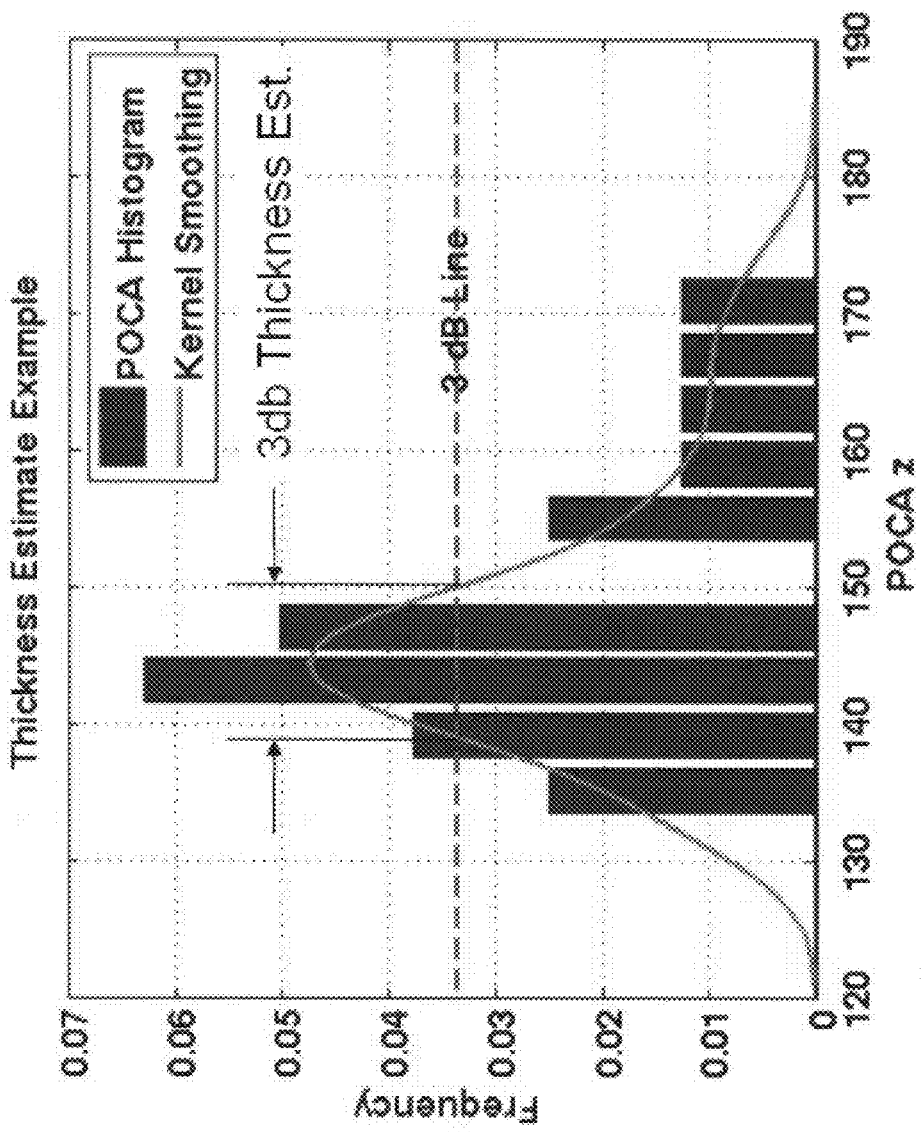
FIG. 5 illustrates an exemplary histogram constructed for a selected bin along z direction (i.e., the thickness direction) as a blue bar graph.

FIG. 5 illustrates an exemplary histogram constructed for a selected bin along z direction (i.e., the thickness direction) as a blue bar graph. To determine the thickness in z in FIG. 5, a kernel smoothing density estimating technique can be used. For example, FIG. 5 illustrates using a Gaussian kernel to smooth the histogram (shown as the green curve in FIG. 5). After smoothing, the thickness can be estimated as the distance between the points on the smoothed density function that fall 3 dB below the maximum value (shown as the dashed horizontal line). This procedure is repeated along each axis x, y or z, and the estimated volume of an assumed rectangular parallelepiped is given by the product of the three size estimates.

In one embodiment, a Figure of Merit (FOM) of a detected object is determined as a measure of the likelihood that the object is truly a high-atomic number material (i.e., a threat object). This FOM value can be defined as the product of the median scattering angle times the total number of scattered charged particles, such as muons, within the estimated volume, and divided by the product of the estimated volume and the total number of particles transiting that volume. In other words, this FOM value is the estimated density of scattering events (number of events divided by the volume) times the median scattering angle of events within the volume. The above FOM determining technique represents only one way to estimate the likelihood that the object is truly a high-atomic number material, and a modification to this FOM estimate is possible. Moreover, for each detected object, a number of other FOMs can be computed. For example, one FOM computes an average scattering density of the object volume. Another FOM computes PoCA density within the object volume. Yet another FOM computes geometric mean of (pθ) of tracks crossing the object volume.

Figure 6:
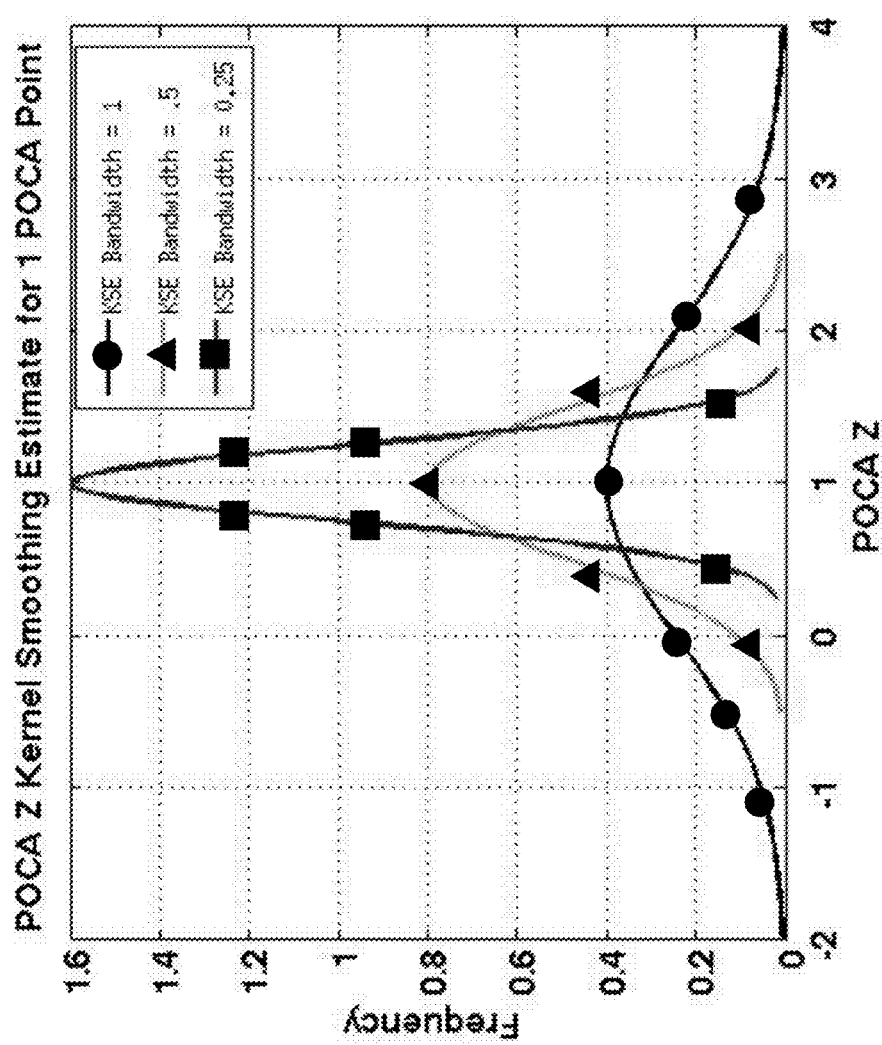
FIG. 6 illustrates three exemplary Gaussian kernels with different full width at half maximum.
Figure 7:
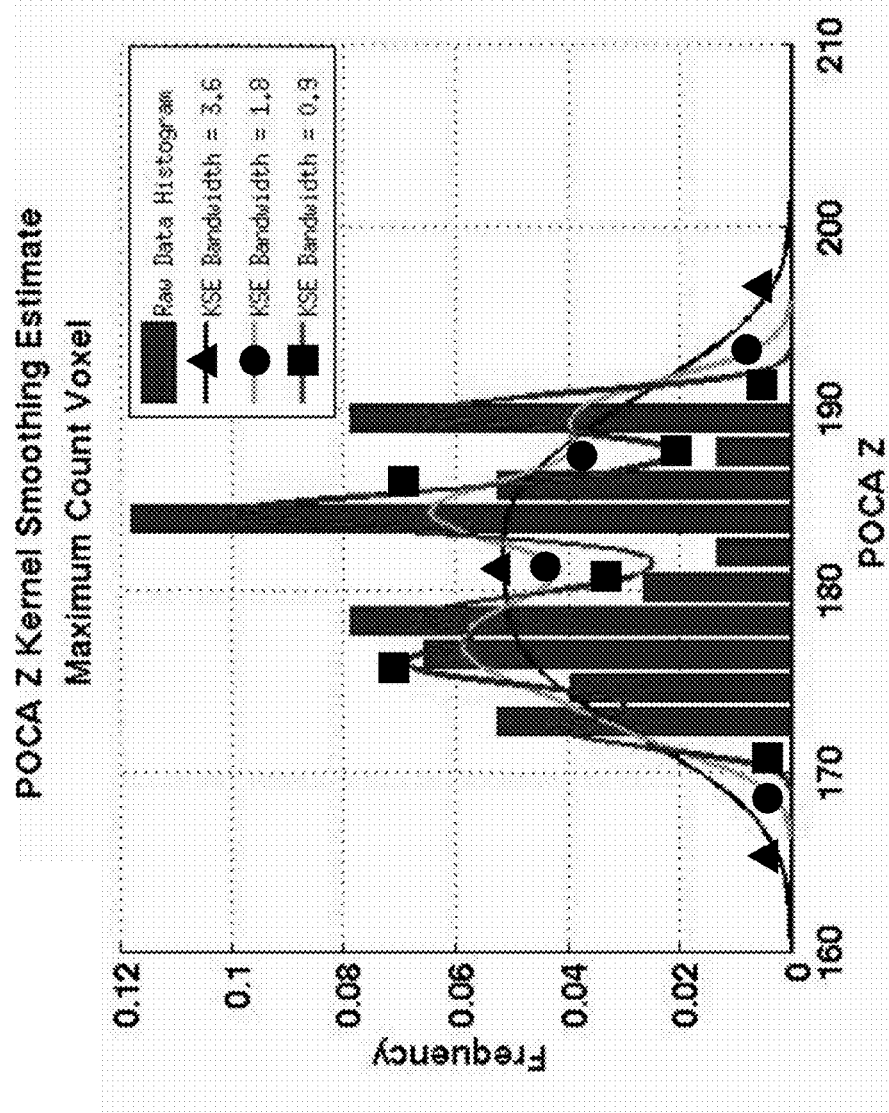
FIG. 7 illustrates an example of applying the three kernels in FIG. 6 to the same exemplary raw histogram in FIG. 5.

When detecting multiple objects, the number of different objects inferred from the above-described histogram calculation technique can depend on the choice of smoothing kernel applied to the histogram. FIG. 6 illustrates three exemplary Gaussian kernels with different full width at half maximum. FIG. 7 illustrates an example of applying the three kernels in FIG. 6 to the same exemplary raw histogram in FIG. 5. As can be seen in FIG. 7, when taking the width at 3 dB below the peaks, the two broadest kernels yield a single object thickness (the intermediate kernel nearly divides the object into two objects), whereas the narrowest kernel yields three distinctive objects. The resulting FOMs may also differ.

Modified Detection Technique for Improved Robustness

Various embodiments of the present technology described above use primarily the detected charged particle tracks, i.e., the PoCA image, as the initial input for object detection. The Center of Mass (CM) location estimate obtained based on these techniques tends to show a systematic shift in position from the location of highest PoCA density to the final estimated location. In an alternative embodiment, in addition to the PoCA image, the reconstructed charged particle image is also used as an input for object detection. This alternative technique can facilitate reducing the CM shift by using the image density as an input.

In one embodiment, the modified detection technique is built onto the above-described objection detection techniques based on the PoCA image. Hence, potential objects within a VOI are first identified based on the PoCA image. Next, the reconstructed charged particle image of the same VOI is obtained. The reconstructed charged particle image is partitioned into voxels, and each voxel of the image is associated with a scattering density denoted by $\lambda$. Next, the CM of the voxels that define each identified potential object can be computed as:

$$CM_{voxel} = (\Sigma \lambda * x)/n_{voxel},$$

where the summation is over the voxels in a region of interest (ROI) both including and in the vicinity of the potential object (e.g., the ROI can include the previously determined object size based on the PoCA technique plus a buffer layer having a user-specified width around the potential object), x is the vector location of the center of each voxel, and $n_{voxel}$ is the number of voxels in the ROI.

After determining the CM, the ROI is moved to center the ROI on the newly computed CM and $\lambda$ for each voxel in the new ROI is extracted. The highest value of $\lambda$ found is designated $\lambda_{max}$. A histogram of $\lambda$ along each axis is plotted, analogously to FIGS. 5 and 7. To find the size of the object in each direction, the technique defines a threshold value of $\lambda$, referred to as "$\lambda_{threshold}$," and the coordinates of the most widely separated voxels with $\lambda > \lambda_{threshold}$ becomes the thickness of the object along that axis. In some practical implementations, $$\lambda_{threshold} = k \times \lambda_{max}$$

where k≈0.66 produces a robust estimator for object thickness. In general, $\lambda_{threshold}$ is chosen by the user. However, it is found that an interval between 0.5 and 0.75 for the coefficient k is likely to include most of the useful values. In one embodiment, after the object size has been determined, the object's location can be specified by defining its center as the centroid of the resulting parallelepiped, using the thicknesses determined along each of the x, y and z axes.

After one or multiple objects have been identified, the object features can be extracted over the spatial extent of each identified object defined by its location and breadth along the x, y and z axes. Such object features can include, but are not limited to: the scattering density and effective atomic number.

In the above described techniques, the output can depend on the user's initial guess for N, the number of separate objects in the VOI, and the choice of smoothing kernel width, among others. In some embodiments, convergence is obtained by maximizing the FOM of an object by varying the smoothing kernel width.

Pre-Selection of Identified Object(s)

In some implementations when a fixed number of objects, M, are to be identified, certain objects, such as small-sized SNM, may be overlooked. Because the object bins identified are sorted by PoCA density, small or isolated objects may not be created within the top M object bins. In order to improve identification of such objects, a larger number of objects, N>M are created. Object features related to the image density are used to select the top M objects to be output. The initial set of N objects is sorted according to the ratio of the object's image density (after removing the expected density contribution from its surrounding) to the expected variation in the surrounding density. Such a ratio provides an estimate of the signal to noise ratio. After sorting, the top M objects are output as the objects of interest.

The disclosed techniques can be incorporated into the software module in Multi-Mode Passive Detection System (MMPDS) to provide improved object identification, localization and characterization.

Figure 8A:
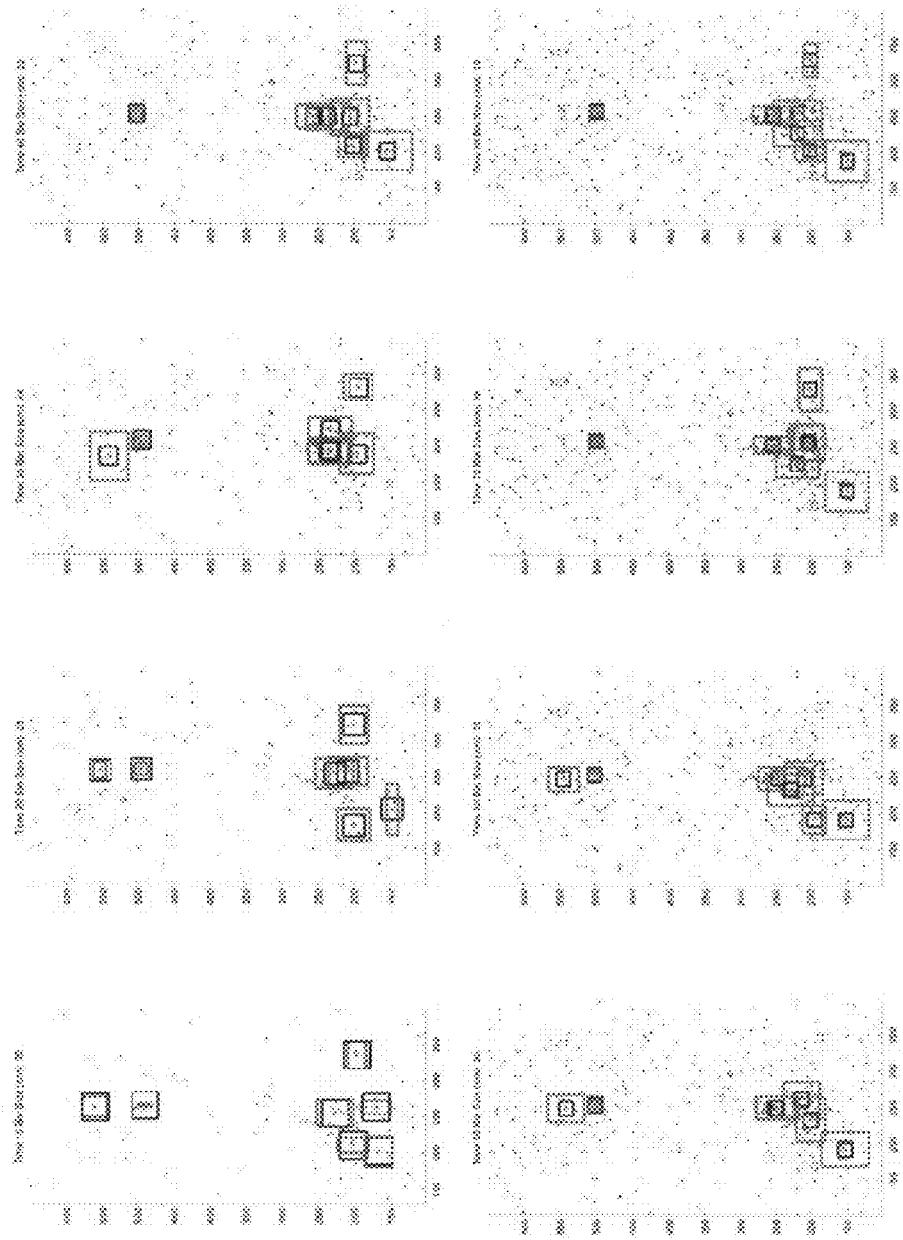
FIGS. 8A-8B show simulated data of a van with several target objects obtained at (muon) scan times ranging from 10 to 120 seconds.
Figure 8B:
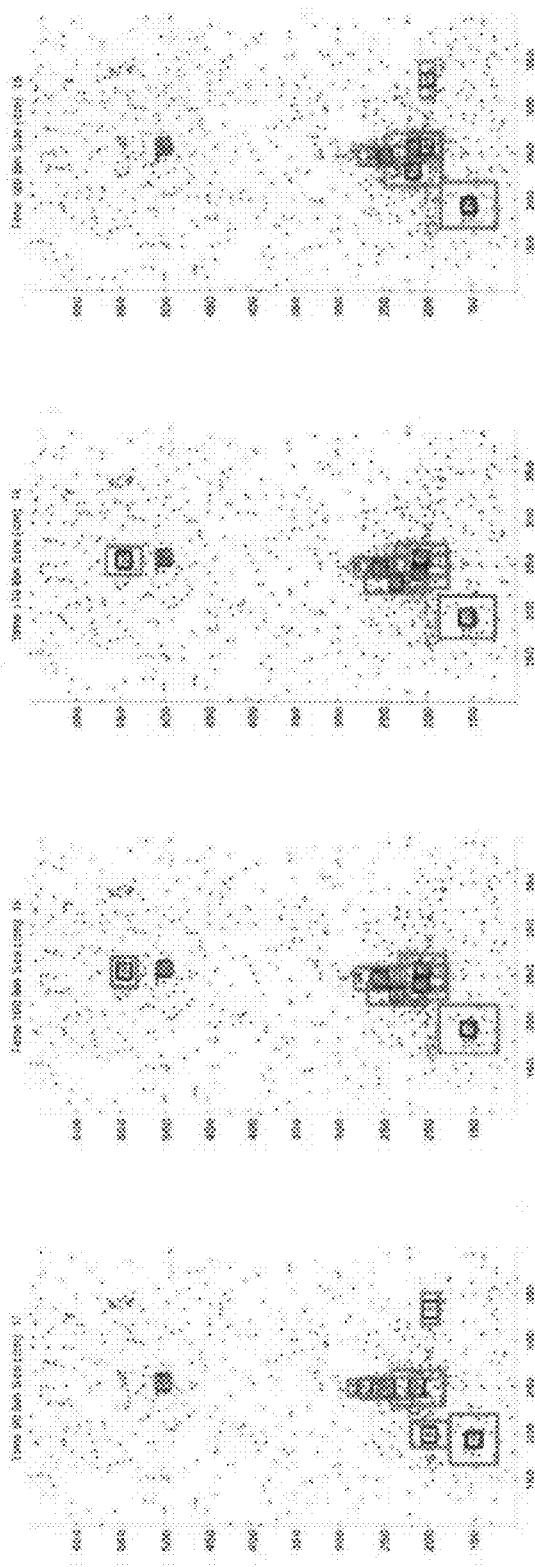

FIGS. 8A-8B show simulated data of a van with several target objects obtained at (muon) scan times ranging from 10 to 120 seconds. Red dots within each plot represent the PoCAs obtained in each scan that fall above the CFAR cutoff value. Black outlines represent the simulated actual target objects, and the green outlines represent the estimates generated by the object detection technique based on analyzing a raw PoCA image.

Figure 9:
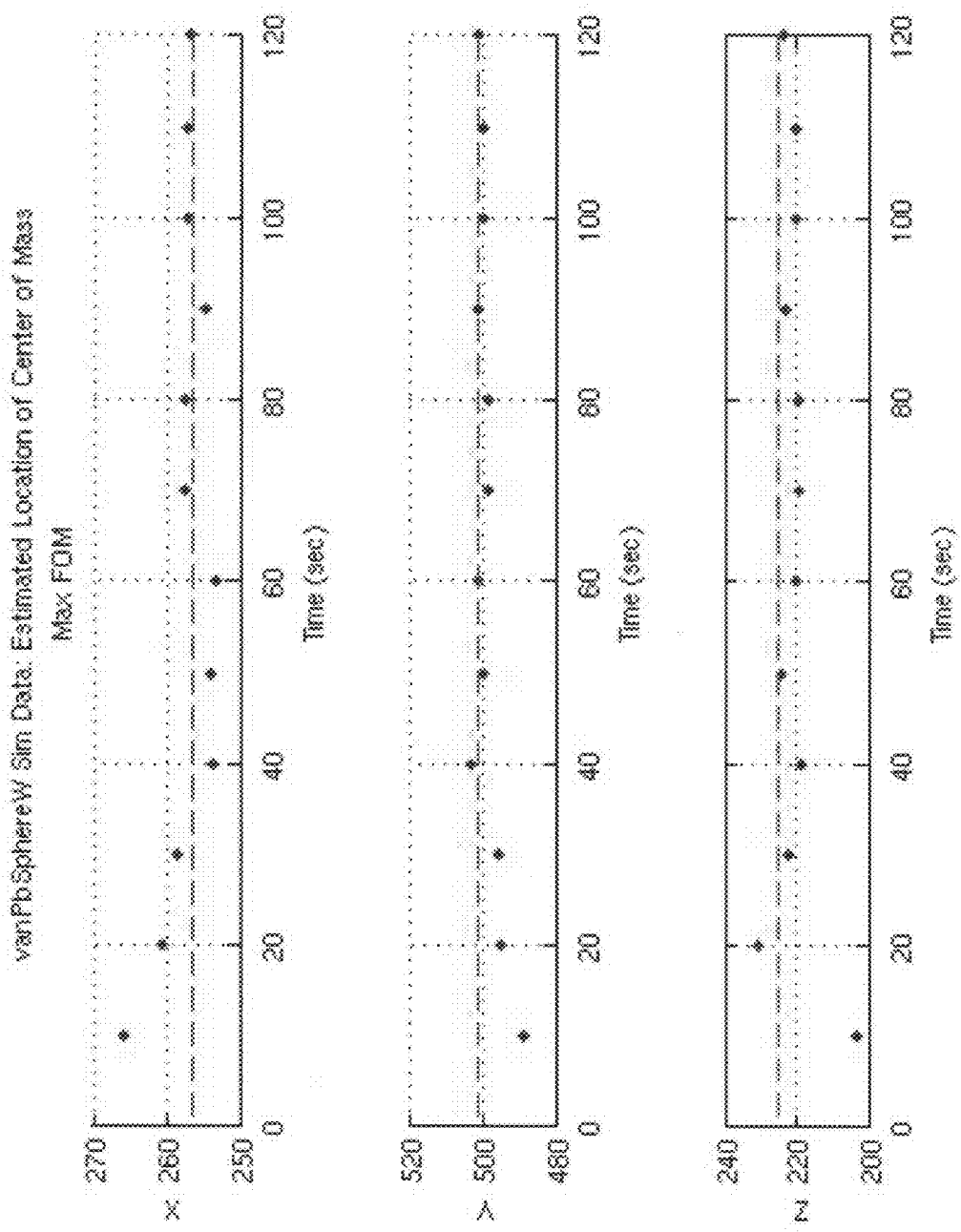
FIG. 9 shows how the estimate of the CM location of the largest (main) target in FIGS. 8A-8B improves as the scan time increases.

FIG. 9 shows how the estimate of the CM location of the largest (main) target in FIGS. 8A-8B, obtained by maximizing the associated FOM, improves as the scan time increases. The subplots in FIG. 9 represent estimates of the x, y and z coordinates of the CM of the main target. Improvement is demonstrated by the reduction in scatter of the estimates with increasing scan time, as well as by convergence to the "ground truth" value represented by the dashed line.

Figure 10:
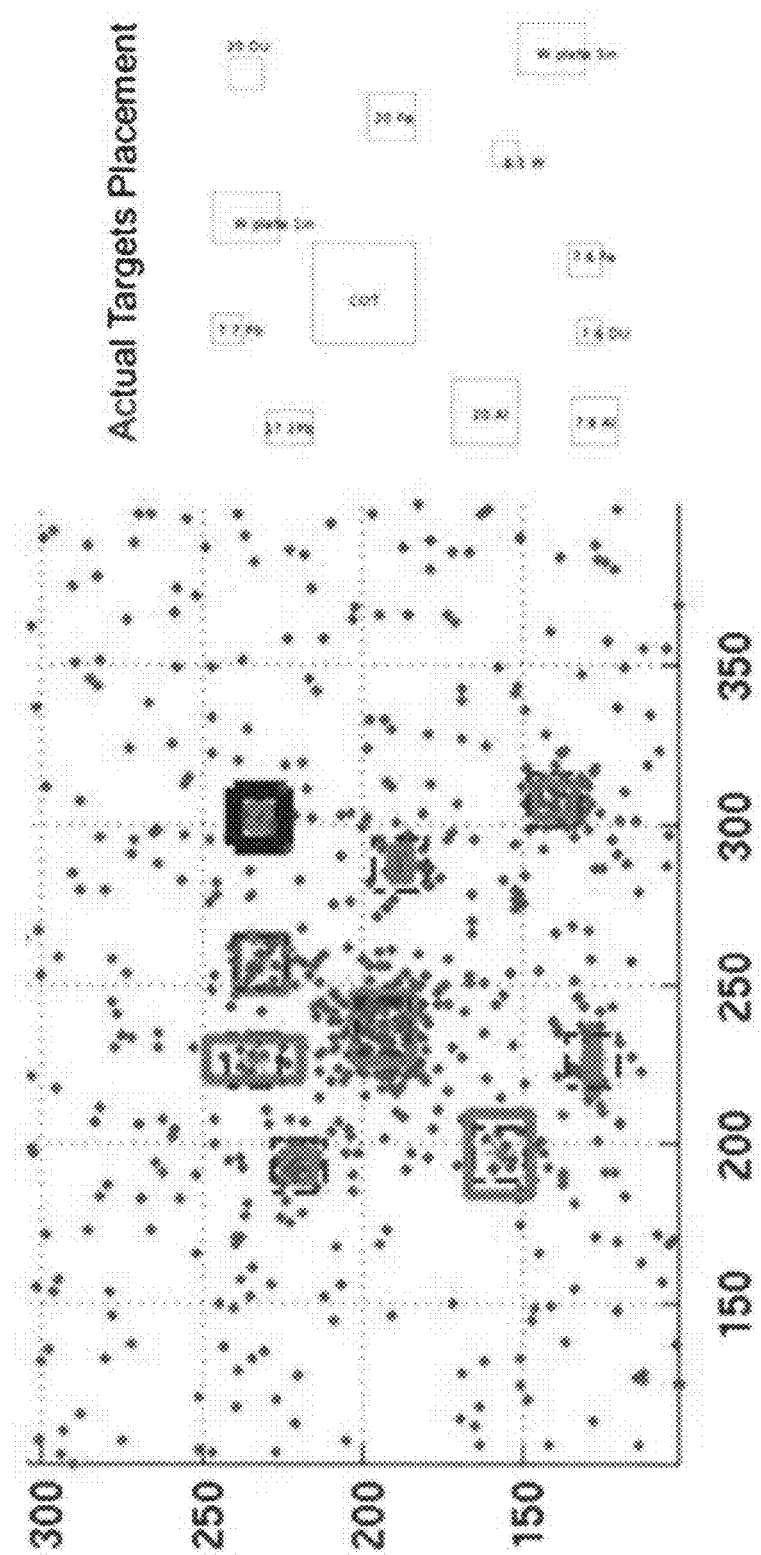
FIG. 10 illustrates exemplary simulation results of the 120-second scan of the van with 12 isolated targets scattered within a VOI.

FIG. 10 illustrates exemplary simulation results of the 120-second scan of the van with 12 isolated targets scattered within a VOI. As shown in FIG. 10, when compared to the actual targets placements, the simulation results robustly detect and localize nine larger objects while the three smallest objects are not detected.

Various embodiments improve the speed and localization ability of MMPDS software, which enables improved nuclear and radiological contraband detection. By improving the probability of detection of distributed SNM and other high-density contraband, and by reducing false alarms, the disclosed technology improves security and throughput at border crossings and other screening checkpoints.

While various examples and implementations of the disclosed object detection and feature extraction techniques are described in the context of the reconstructed muon images, these disclosed techniques are also applicable to analyzing reconstructed cosmic-ray electron images and other reconstructed charged particle images obtained from other types of cosmic-ray tomography systems. Moreover, the disclosed techniques are also applicable to analyzing reconstructed active electron (i.e., using active electron sources) scanning images or active proton (i.e., using active proton sources) scanning images, and other charged particle scanning images obtained from other types of active charged particle tomography systems. Hence, the disclosed techniques are not limited to analyzing reconstructed muon images.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document and attached appendices contain many specifics, these should not be construed as limitations on the scope of any invention or of what may be claimed, but rather as descriptions of features that may be specific to particular embodiments of particular inventions. Certain features that are described in this patent document and attached appendices in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attached appendices should not be understood as requiring such separation in all embodiments.

Only a few implementations and examples are described and other implementations, enhancements and variations can be made based on what is described and illustrated in this patent document and attached appendices.

What is claimed is:

1. A method for analyzing a point of closest approach (PoCA) image of a volume of interest (VOI) to detect one or more objects within the VOI, the method comprising:
   detecting a plurality of charged particles using a charged particle detector and obtaining a set of recorded PoCA points based on the detected charged particles;
   partitioning the VOI into a set of bins wherein each bin includes a subset of PoCA points of the set of recorded PoCA points;
   calculating a bin metric for each bin in the set of bins, wherein the bin metric for each bin includes a median effective scattering angle;
   selecting a subset of bins in the set of bins based on the calculated bin metric, wherein the subset of bins is most likely to contain objects; and
   determining a potential object for each of the selected subset of bins by determining a location and a size for the potential object based at least on the PoCA points inside the bin.

2. The method of claim 1, wherein the set of bins include equally-sized bins, and wherein the size of the bins is determined such that each of the set of bins contains on-average a same number of PoCA points, wherein the same number is a user-defined value.

3. The method of claim 1, wherein the median effective scattering angle is calculated at least by:
   calculating a product of a particle momentum and an associated scattering angle for each PoCA within the bin; and
   calculating a median of the calculated products of the subset of PoCA points within each bin.

4. The method of claim 1, wherein selecting the subset of bins in the set of bins based on the calculated bin metric includes selecting the top N bins in the set of bins with a highest product between scattered charged particles and the median effective scattering angle.

5. The method of claim 4, wherein the subset of bins includes non-adjacent bins.

6. The method of claim 4, wherein N is a user-selected number chosen to be large compared to the number of separate objects that are expected in the VOI, wherein the number of separate objects includes threatening objects, non-threatening objects of interest, and other non-threatening objects.

7. The method of claim 1, wherein determining the location for a potential object includes determining a center of mass (CM) of each of the selected bin based on a momenta and scattering angles associated with the PoCA points inside the selected bin and PoCA points in the surrounding bins around the selected bin.

8. The method of claim 7, wherein after determining the CM for a selected bin, the method further comprises:
   re-centering the selected object to the location of the determined CM; and
   re-calculating the bin metric for the selected object.

9. The method of claim 1, further comprising:
   filtering the set of recorded PoCA points to remove low value PoCA points corresponding to low scattering density prior to determining the size for a potential object.

10. The method of claim 9, wherein filtering the set of recorded PoCA points to remove low value PoCA points includes determining a cutoff value for a product of a particle momentum and a scattering angle for a given PoCA point.

11. The method of claim 10, wherein determining the cutoff value includes selecting PoCA points falling in a highest range of an expected distribution to achieve a user-specified constant false alarm rate.

12. The method of claim 10, further comprising:
   after filtering the set of recorded PoCA points, calculating the bin metric for a selected bin as the product of the median effective scattering angle and the number of charged particles in the selected bin, wherein the bin metric indicates the likely density and atomic number of the selected bin.

13. The method of claim 1, wherein determining the size for a potential object includes determining a size separately for each of the x, y, and z directions, and for each direction:
   constructing a histogram of the PoCA points inside the associated bin based on a product of a particle momentum and a scattering angle for each of the PoCA points inside the associated bin;
   applying a smoothed density function on the histogram; and
   measuring a distance between points on the smoothed density function that fall a predetermined value below the maximum value.

14. The method of claim 13, wherein the predetermined value is substantially 3 dB.

15. The method of claim 1, further comprising:
   after determining the potential object for each of the selected subset of bins, determining a figure of merit (FOM) of the potential object as a measure of the likelihood that the potential object is truly a target object.

16. The method of claim 15, wherein the FOM value is determined as the product of the median effective scattering angle times the total number of scattered charged particles within the potential object and divided by the product of the estimated volume of the potential object and the total number of particles transiting the volume.

17. The method of claim 16, wherein the FOM value is an estimated density of scattering events times the median effective scattering angle of the events within the volume of the potential object.

18. The method of claim 1, further comprising:
   while calculating the bin metric for each bin in the set of bins, mitigating bin edge effect by performing the following:

shifting each bin by a portion of the linear dimension of the bin along each of the three axes x, y and z;
calculating the bin metric for each of the shifted bins and an unshifted bin; and
assigning a highest calculated bin metric among the shifted bins and the unshifted bin to the unshifted bin.

19. The method of claim 1, further comprising correcting a shift of the center of mass location of a determined potential object from the location of the highest PoCA density.

20. The method of claim 19, wherein correcting the shift of the center of mass location of the determined potential object includes:
obtaining a reconstructed charged particle image of the VOI, wherein the reconstructed charged particle image is partitioned into a set of voxels, and wherein each voxel is associated with a scattering density;
computing a modified center of mass location for the determined potential object based on both a first set of voxels occupying the volume of the determined potential object and a second set of voxels occupying a layer surrounding the determined potential object; and
moving the determined potential object to center on the modified center of mass location.

21. The method of claim 20, wherein computing the modified center of mass location based on the first set of voxels and the second set of voxels involves computing a summation over the first and second sets of voxels of a product of the associated scattering density of each voxel and the vector location of the center of each voxel.

22. A system for analyzing a point of closest approach (PoCA) image of a volume of interest (VOI) to detect one or more objects within the VOI, the system comprising:
a processor;
a memory; and
an image processing mechanism communicatively coupled to the processor and the memory, wherein the image processing mechanism is configured to:
detect a plurality of charged particles using a charged particle detector and obtain a set of recorded PoCA points based on the detected charged particles;
partition the VOI into a set of bins wherein each bin includes a subset of PoCA points of the set of recorded PoCA points;
calculate a bin metric for each bin in the set of bins, wherein the bin metric for each bin includes a median effective scattering angle;
select a subset of bins in the set of bins based on the calculated bin metric, wherein the subset of bins is most likely to contain objects; and
determine a potential object for each of the selected subset of bins by determining a location and a size for the potential object based at least on the PoCA points inside the bin.

23. The system of claim 22, wherein the charged particle images include:
a cosmic-ray muon image;
a cosmic-ray electron image; or
a combined cosmic-ray muon and cosmic-ray electron image.

24. The system of claim 22, wherein the image processing mechanism is configured to further, while calculating the bin metric for each bin in the set of bins, mitigate a bin edge effect by performing the following:
shifting each bin by a portion of the linear dimension of the bin along each of the three axes x, y and z;
calculating the bin metric for each of the shifted bins and an unshifted bin; and
assigning a highest calculated bin metric among the shifted bins and the unshifted bin to the unshifted bin.

25. The system of claim 22, wherein the image processing mechanism is configured to further correct a shift of the center of mass location of a determined potential object from the location of the highest PoCA density.

26. The system of claim 25, wherein correcting the shift of the center of mass location of the determined potential object includes:
obtaining a reconstructed charged particle image of the VOI, wherein the reconstructed charged particle image is partitioned into a set of voxels, and wherein each voxel is associated with a scattering density;
computing a modified center of mass location for the determined potential object based on both a first set of voxels occupying the volume of the determined potential object and a second set of voxels occupying a layer surrounding the determined potential object; and
moving the determined potential object to center on the modified center of mass location.

27. A system for using cosmic ray-generated charged particles to inspect objects in an object holding area, comprising:
a first set of position sensitive particle detectors located on a first side of an object holding area to measure positions and directions of incident charged particles towards the object holding area that are caused cosmic rays;
a second set of position sensitive particle detectors located on a second side of the object holding area opposite to the first side to measure positions and directions of outgoing charged particles exiting the object holding area; and
a signal processing unit to receive data of measured signals of the incident charged particles from the first set of position sensitive particle detectors and measured signals of the outgoing charged particle from the second set of position sensitive particle detectors, the signal processing unit is configured to analyze scattering behaviors of the charged particles caused by scattering of the charged particles within the object holding area based on the measured incoming and outgoing positions and directions of the charged particle to construct a point of closest approach (PoCA) image of a volume of interest (VOI) within the object holding area comprising a set of recorded PoCA points from the received data,
wherein the signal processing unit is configured to analyze the PoCA image to detect one or more objects within the VOI and performs:
partitioning the VOI into a set of bins wherein each bin includes a subset of PoCA points of the set of recorded PoCA points;
calculating a bin metric for each bin in the set of bins, wherein the bin metric for each bin includes a median effective scattering angle;
selecting a subset of bins in the set of bins based on the calculated bin metric, wherein the subset of bins is most likely to contain objects; and
determining a potential object for each of the selected subset of bins by determining a location and a size for the potential object based at least on the PoCA points inside the bin.

28. The system of claim 27, wherein the charged particles include muons or electrons.

29. The system of claim 27, wherein the first and the second sets of position sensitive particle detectors detect both muons and electrons.

30. The system of claim 27, wherein the first or the second set of position sensitive particle detectors includes drift tubes arranged to allow at least three charged particle positional measurements in a first direction and at least three charged particle positional measurements in a second direction different from the first direction.

31. The system of claim 27, wherein the signal processing unit is configured to further, while calculating the bin metric for each bin in the set of bins, mitigate a bin edge effect by performing the following:
   shifting each bin by a portion of the linear dimension of the bin along each of the three axes x, y and z;
   calculating the bin metric for each of the shifted bins and an unshifted bin; and
   assigning a highest calculated bin metric among the shifted bins and the unshifted bin to the unshifted bin.

32. The system of claim 27, wherein the signal processing unit is configured to further correct a shift of the center of mass location of a determined potential object from the location of the highest PoCA density.

* * * * *

UNITED STATES PATENT AND TRADEMARK OFFICE
CERTIFICATE OF CORRECTION

PATENT NO. : 10,215,717 B2
APPLICATION NO. : 14/839883
DATED : February 26, 2019
INVENTOR(S) : Priscilla Kurnadi et al.

It is certified that error appears in the above-identified patent and that said Letters Patent is hereby corrected as shown below:

In the Specification

In Column 7, Line 37, delete "$\Delta\theta=0.078.$" and insert --$\Delta\theta=0.07\theta.$--, therefor.

Signed and Sealed this
Nineteenth Day of November, 2019

Andrei Iancu
*Director of the United States Patent and Trademark Office*